(12) United States Patent
Hanberger (10) Patent No.: US 9,936,744 B2
(45) Date of Patent: Apr. 10, 2018

(54) TUNIC INTENDED TO BE WORN BY A PATIENT UNDERGOING INFUSION THERAPY, FOR USE PARTICULARLY BY CHILDREN

(76) Inventor: Martin Hanberger, Johanneshov (SE)

( * ) Notice: Subject to any disclaimer, the term of this patent is extended or adjusted under 35 U.S.C. 154(b) by 1106 days.

(21) Appl. No.: 14/122,989

(22) PCT Filed: May 30, 2012

(86) PCT No.: PCT/SE2012/050578
§ 371 (c)(1),
(2), (4) Date: Feb. 25, 2014

(87) PCT Pub. No.: WO2012/166043
PCT Pub. Date: Dec. 6, 2012

(65) Prior Publication Data
US 2014/0165255 A1 Jun. 19, 2014

(30) Foreign Application Priority Data
May 31, 2011 (SE) ...................................... 1150509

(51) Int. Cl.
*A41D 13/12* (2006.01)
*A61M 5/142* (2006.01)
(52) U.S. Cl.
CPC ..... *A41D 13/1245* (2013.01); *A41D 13/1281* (2013.01); *A61M 5/14244* (2013.01); *A61M 2205/3576* (2013.01); *A61M 2205/50* (2013.01); *A61M 2205/587* (2013.01); *A61M 2205/8206* (2013.01); *A61M 2209/088* (2013.01)

(58) Field of Classification Search
CPC ........... A41D 13/1245; A41D 13/1281; A61M 5/14244; A61M 2205/3576; A61M 2205/50; A61M 2205/587; A61M 2205/8206; A61M 2209/088
See application file for complete search history.

(56) References Cited

U.S. PATENT DOCUMENTS

| 4,087,864 A | * | 5/1978 | LaBove | A41D 13/1245 2/102 |
| 4,666,432 A | * | 5/1987 | McNeish | A61M 25/02 128/DIG. 26 |
| 5,708,978 A | * | 1/1998 | Johnsrud | A41D 13/1245 2/102 |

(Continued)

FOREIGN PATENT DOCUMENTS

AU  2007100122 A4  3/2007

OTHER PUBLICATIONS

International Search Report for PCT:SE2012:050578, dated Feb. 4, 2012.
Written Opinion for PCT:SE2012:050578, completed Sep. 3, 2012.

*Primary Examiner* — Shaun R Hurley
*Assistant Examiner* — Andrew W Sutton
(74) *Attorney, Agent, or Firm* — Brinks Gilson & Lione (57) ABSTRACT

A tunic includes pockets to accommodate infusion equipment. Each pocket for accommodating infusion equipment is formed as an openable storage compartment from a textile material and a semi-rigid spacer layer material arranged in the textile material. The semi-rigid spacer layer material maintains its form so that each pocket stores infusion equipment in a comfortable well-protected and discreet manner.

20 Claims, 4 Drawing Sheets

(56) References Cited

U.S. PATENT DOCUMENTS

| | | | | |
|---|---|---|---|---|
| 2004/0226073 A1* | 11/2004 | McCullar | ............ | A41D 13/1245 2/114 |
| 2009/0031467 A1* | 2/2009 | Swindells | ........... | A41D 13/0012 2/51 |
| 2015/0374048 A1* | 12/2015 | Theodossiou | ....... | A41D 13/1245 2/114 |
| 2016/0199576 A1* | 7/2016 | Savage | ................. | A61B 5/6805 604/66 |

* cited by examiner

TUNIC INTENDED TO BE WORN BY A PATIENT UNDERGOING INFUSION THERAPY, FOR USE PARTICULARLY BY CHILDREN

RELATED APPLICATIONS

This application claims the benefit under 35 U.S.C. § 371 of international Patent Application No. PCT/SE2012/050578, having an international filing date of May 30, 2012, which claims priority to Swedish Application No. 1150509-6, flied May 31, 2011, the contents of both of which are incorporated herein by reference in their entirety.

The present invention concerns a tunic intended to be worn by a patient undergoing infusion therapy, the patient may be in particular a child. The tunic is intended to be worn on the patient's upper body, covering the patient's life or the torso. The tunic is made of fabric and provided with cavities which are formed of, in relation to the fabric, substantially stiffening inlay materials which from the patient to the outside is substantially cup or tray-shaped. In what areas can be occupied and in a protective manner housed units forming part of common infusion units for parenteral administration of drugs to a patient. The invention also relates to a use of such a tunic in a system for administration of infusion therapy with infusion equipment comprising a radio transmitter that allows remote-controlled controlling and monitoring the operating state of the infusion equipment.

"Parenteral" administration of medication or fluid describes the supply of medications without them passing through the gastro-intestinal tract. Many types of parenteral administration require the continuous supply of the medication or fluid, rather than individual or repeated injections. Medications or other types of pharmaceutical agent must, therefore, be continuously supplied during long periods, in some cases as long as several years. The term "medication" as it is used here describes in principle any physiologically or pharmacologically active substance used to achieve a local effect at the site of administration or a systemic effect at a location distant from the site of administration. The term "infusion therapy" is here used to denote the process of a patient receiving intravenous treatment. The advantages that are gained by continuous therapy can comprise a reduction in toxic and other undesired effects that are related to limiting doses of medication, a significant improvement of the efficiency of the therapy, and an increase in the well-being of the patient. The traditional way of administrating parenteral treatment with delayed release is an intravenous drip. While this may be fully acceptable in a hospital setting, it limits the freedom of motion of the recipient significantly. As a result of this, significant research has been devoted in recent years to the development of small, portable infusion arrangements. In order for long-term infusion therapy to be successful, the infusion arrangement must be acceptable to the carrier. Arrangements that are clumsy, heavy, uncomfortable or dominating, that limits the lifestyle or appearance of the user in another manner, or that require complicated methods of monitoring will not be readily accepted. This is particularly the case when the user or patient is a child. The term "child" is used below to denote individuals younger than 18 years. The individuals who most readily come into question in the following description are children, who have different needs, fears and expectations, depending on age. The same is true for the parents of a sick child, whose life situation will be considerably influenced during the relatively long period during which the child is receiving treatment. What is common for children in the ages 2-5, 6-11 and 12-17 is that they generally have an active lifestyle and the need to participate in play with other children. In particular children in the third group of slightly older children, have, in addition, often become more conscious of their appearance, with a desire to feel independent, and not to deviate from or differ from their contemporaries.

It is known that children respond more poorly to the medications given by both infusion therapy and in general than adults, and thus they require also more extensive and longer-lasting treatments. There is, of course, throughout the complete period of treatment a need for play with children of the same age, and for the possibility to participate in various activities. Therapeutic treatment through the parenteral administration of medication, in particular to children, normally includes very long durations, up to 2-3 years.

Known arrangements for the administration of infusion therapy to a patient normally include a frame, such as a cart, provided with wheels, which frame has an upper holder on which a flow delivery system with hangers for containers of infusion fluid are arranged. The patient can, due to the wheels, move within a limited region by drawing the cart along with himself or herself.

From U.S. Pat. No. 4,087,864 is known a vest of textile material which is intended to be worn by a patient undergoing infusion therapy and which allows the patient to move around during the treatment. The vest is in the front provided with a number of channel-shaped textile pockets formed outside of which some of said external pockets having openings at both the top to bottom. Each pocket forms a storage space for partly visibly supporting a respective unit of the set of devices, connected by lines, are part of infusion equipment. Among said devices can for example be mentioned; a bag containing drugs, a pump and a battery. The pockets which are open at the bottom can be closed by a buckle in the form of a strip of fabric is provided with Velcro strips. Function and status of the units that are only partially occupied in the pockets can be done through observation and direct visual control, because the devices are so carried on the vest that they at least are partially visible in the outer pockets.

It should be understood that the known vest with its many open outside pockets would limit a user's lifestyle and appearance not only to an adult but also a child. In particular, it should be understood that a child wearing the vest will be restricted or inhibited in their play wherein said outer pockets, containing relatively heavy unprotected infusion equipment, likely can snag on and get caught in play or in worst cases even break. In addition, the vest with large numbers of outside pockets with at least partially, visibly busy infusion equipment tend to be eye catching and be anything but subtle with the result that the child might feel different from its peers and thus uncomfortable with the vest.

There is consequently a need for comfortable, compact and discrete portable tunic for the administration of infusion therapy that do not disturb the lifestyle or appearance of the user. In particular, there is a need of a tunic for children that protects sensitive equipment accommodated in the tunic and makes it possible for the patient to participate in play in an active manner during the treatment, without the observation of the immediate physical vicinity of the hospital staff even during an ongoing and often long-term treatment. It is, however, important that hospital personnel and other responsible personnel can ensure that the correct medication is supplied efficiently to each patient, in the correct dose, at the correct time. In which there is a desire that monitoring can take place even if the patient is outside the hospital setting and busy with activities that are part of the persons normal lifestyle.

The aim of the present invention is to achieve a tunic that can be carried on the body for the administration of infusion therapy to a patient, who may be, in particular, a child. The tunic is to make it possible to carry out infusion treatment without noticeably troubling the patient or user, and without limiting the patient's lifestyle or appearance.

This purpose is achieved through a tunic demonstrating the distinctive features that are stated in claim 1. Further advantages of the invention are made clear by the dependent claims.

It has surprisingly been found that the present tunic for infusion therapy is highly suitable for use in combination with any known system for the administration of infusion therapy which allows remote-controlled monitoring and control of infusion equipments operating state. As already mentioned, for a prolonged infusion therapy to be successful, it is of importance that the infusion device may be acceptable to the wearer. Through a combination of the present tunic exhibiting in the fabric integral stiffening portions defining storage space with the possibility of a secure and discreet (invisible), to carry infusion equipment on the body, and a system of administration of infusion therapy, which allows remote-controlled monitoring and control of infusions equipment provides the patient carrying this tunic a number of advantages. Among other things, the patient is given the opportunity to move, not only in the immediate hospital environment but can the patient with the necessary comfort and substantially conserved lifestyle also operate outside the hospital environment.

The invention will be described below in more detail with reference to the attached drawings, of which.

FIGS. 1-4 show an overview of a tunic for the administration of infusion therapy to a patient, who may be, in particular, a child. The tunic is designed with the body shape of the patient and of a textile that is adapted to the shape of a patient's body. The term "tunic" is here used to denote a garment that covers the waist or trunk of the user or patient, such as a jacket without sleeves or a waistcoat. The tunic has a front piece 1 and a rear piece 2 that are joined to each other along the shoulder lines 3 and 4 and along the body lines 5 and 6. The tunic is provided with a opening 10 for the neck, openings 11 for the arms and an opening 12 for the lower body. The tunic is manufactured from commercially available knitted fabric that allows the garment to be formed to the body of the patient in order to offer high comfort. It is intended that the tunic be worn on top of the patient's existing clothes as an external garment, and to fit closely to the existing clothes. In the centre of the front, the tunic is provided with a zip 15 or similar access arrangement that can be closed, which makes it easy to put the tunic on and to take it off. Other conceivable closing systems that allow the tunic to be taken off may include mechanical closing arrangements of hook-and-eye type, hook-and-loop tape (such as VELCRO®) and adhesive tape. It is expected that the tunic will be manufactured in three or four standard sizes, such as "Small", "Medium", "Large" and "Extra Large", and that it will be possible for both male and female patients to wear tunics of the same basic type.

The tunic is built up, at least in certain areas, from several layers of web 20:1-20:n laid on top of each other, and sewn to each other. Standard classes of web, such as knitted, woven or fabric textiles, are used as starting material. Webs that allow good ventilation and the wicking of moisture are to be preferred, since these are experienced by the patient as being more comfortable with respect to freedom of movement and comfort.

According to the invention, the front 1 and rear 2 pieces of the tunic are provided with pockets intended to form various types of storage compartment. The front piece 1 is sewn as a double piece of two layers 20:1-20:2 laid one on top of the other, of which the outer woven layer 20:2 is so cut that a first pair of pockets 25, 26 is formed low down on the front piece 1, and from which a first pair of storage compartments 30, 31 is located one on each side of the zip and accessible from the said pockets, and a second relatively large storage compartment 32 having the nature of a rucksack is arranged at the rear piece 2. A child can carry and store various objects in the said pockets 25, 26. The second storage compartment at the rear piece 2 can be opened and closed with a zip 35 sewn into the web and running essentially around the complete storage compartment 32.

Figure 1:
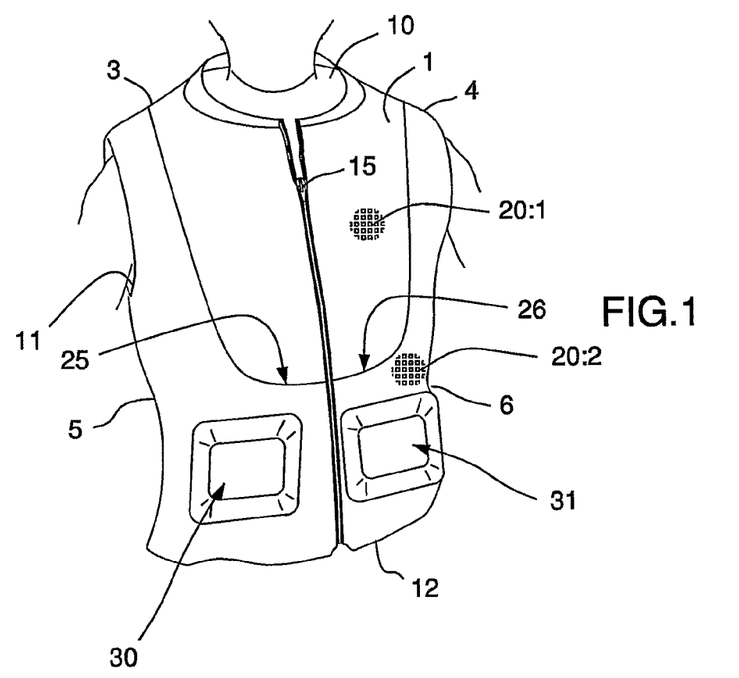
FIG. 1 shows a view from the front of a tunic according to the invention.
Figure 2:
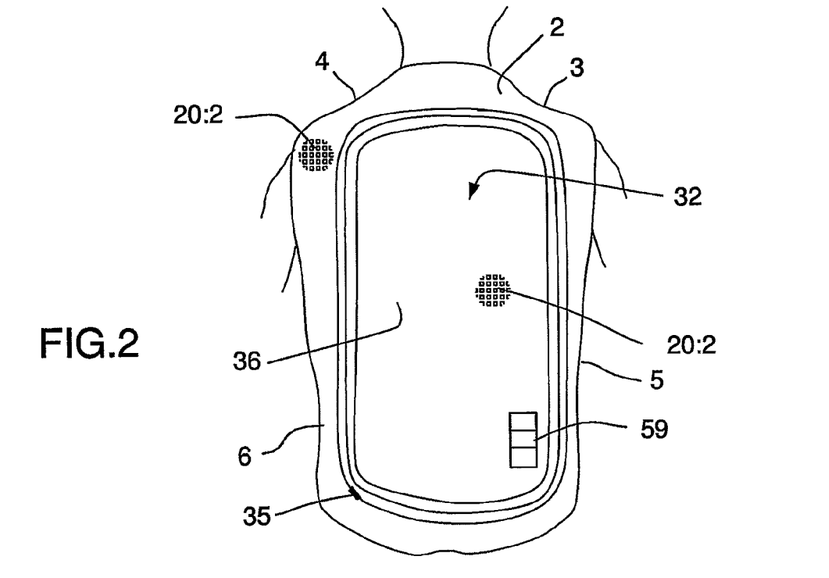
FIG. 2 shows a view from behind of the tunic according to invention.
Figures 3, 4:
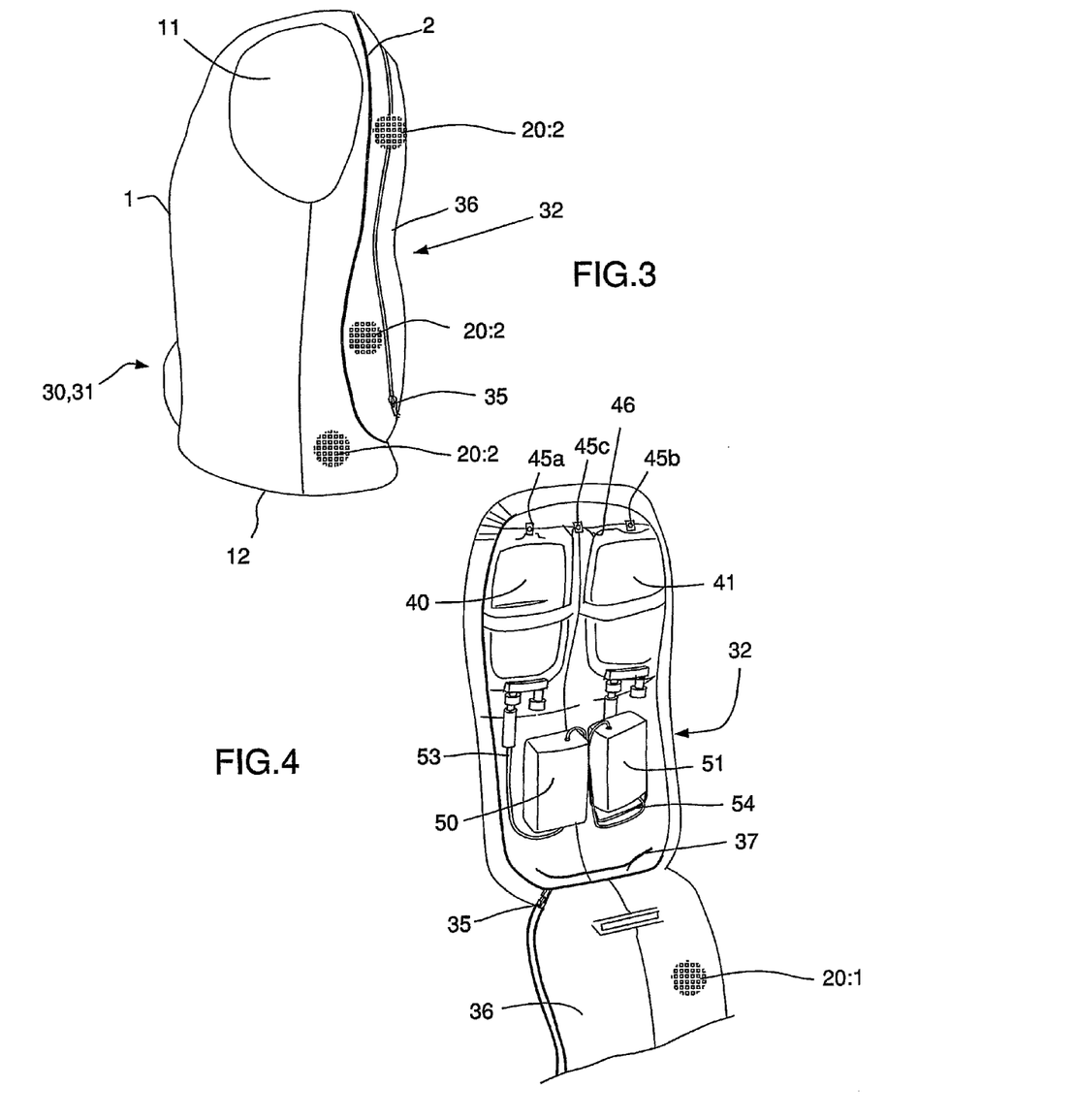
FIG. 3 shows a view from the side of a tunic according to invention.
FIG. 4 shows a perspective view from behind of a tunic, with a compartment having the nature of a rucksack that is part of the unit, in an open condition.

FIG. 4 makes it clear that the second storage compartment 32 at the rear piece 2 is limited outwards by a cover 36 that can be opened downwards. When the pocket is in its open condition, the cover 36 can be opened backwards and downwards as is shown in the drawing, in the manner of a hinge anchored through a seam or through a continuous piece of fabric at the bottom 37 of the storage compartment 32. Since the said cover 36 opens backwards and outwards, it is easy to gain access to the second storage compartment 32, which is located at the rear, from the outside.

Each one of the said first pair of storage compartments 30, 31 at the bottom of the front piece is assigned stiffeners, as is also the second storage compartment 32 at the rear piece 2. The stiffeners are designed as essentially trough-shaped, outwardly bowed spacer layers 40, 41, 42 of "semi-stiff" plastic material. These spacer layers are located, as core material, in special compartments formed between the layers of web, which are placed one on top of each other, whereby it should be realised that the layers with webs and spacer material can be joined to each other, at least in certain regions, such that the resulting component forms a laminate or a laminated web. The said spacer layers 40, 41, 42 are selected from among materials that demonstrate a certain degree of stiffness in combination with bendability and flexibility such that the material is also shock-absorbent, to a certain extent, and thus it offers the possibility, albeit a limited possibility, of adapting to the forms and contours of the human body. See also FIG. 5. The expression "semi-stiff spacer material" is used in the following to denote a material that can be formed, that is shock-absorbent, and that is flexible in a yielding manner. It is an advantage that the spacer material be constituted by foamed plastic material, i.e. of the type that demonstrates a large void volume and low density. It is an advantage that this partially formable and relatively soft foamed plastic material be constituted by a suitable polymer plastic of cross-linked type, for example polyethylene (PEX). The combination of webs with intermediate spacer layers 40, 41, 42 of foamed material of thermoplastic has proved to be particularly suitable for creating compartments intended to house fragile equipment while at the same time offering comfort to the wearer. Due to the spacer layers being located between the layers of web, the tunic is experienced by both the wearer and by those around as any other garment at all, such as a comfortable and warm waistcoat.

FIGS. 3 and 4 show in more detail the first pair of storage compartments 30, 31 at the bottom of the front piece 1 and the second storage compartment 32 at the rear piece 2. An infusion unit is located in the second storage compartment 32, which infusion unit principally comprises a first 40 and a second 41 infusion bag, which infusion bags contain medication and are of transparent plastic material with inlet and outlet channels, and containing the medication that is to be dispensed to the patient. Each one of the infusion bags 40, 41 is suspended from a holder 45a, 45b at the upper part of the rear piece 2 and from an intermediate third common holder 45c that provides additional support. Each of these holders comprises a button, respectively, that is sewn attached by a short strip of fabric at the inner surface of the upper part 46 of the second storage compartment 32, whereby each infusion bag 40, 41 is pressed in place through the button such that the membrane of each infusion bag is oriented in the downwards direction. A first 50 and a second 51 infusion pump are arranged under the infusion bags 40, 41, which pumps can be adjusted independently of each other. The infusion bags 40, 41 are connected to the infusion pumps 50, 51 by flexible fluid lines 53, 54 and by suitable connectors to a central outlet line 55 for the flow of fluid, which central outlet line is connected through a catheter (not shown in the drawings) to the patient for the parenteral supply of medication. As is made most clear by FIG. 5, the central outlet line 55 is located in a discrete manner such that it is guided through an opening in the rear piece 2 and through the flexible cover 70, which reduces the risk that the line will become entangled with an object during, for example, children's play. The fluid line elements 53, 54 support selected contacts for joining, such as screw-on Luer connectors. Batteries 60, 61, one on each side, or similar sources of power are intended to be carried in the two first and second storage compartments 30, 31 at the bottom of the front piece 1 of the tunic, see also FIG. 5. These two batteries 60, 61 are electrically connected to the infusion pumps through a wire 62. Due to the fact that the batteries 60, 61, the infusion pumps 50, 51 and the infusion bags 40, 41 are located at the front and the back of the patient, respectively, i.e. on opposite sides, equilibrium is obtained with respect to the weight of pumps and infusion bags, and thus good balance is obtained for the entirety of the unit that does not noticeably trouble the patient, acting instead as lightening the load on the back, shoulders and neck.

Figure 5:
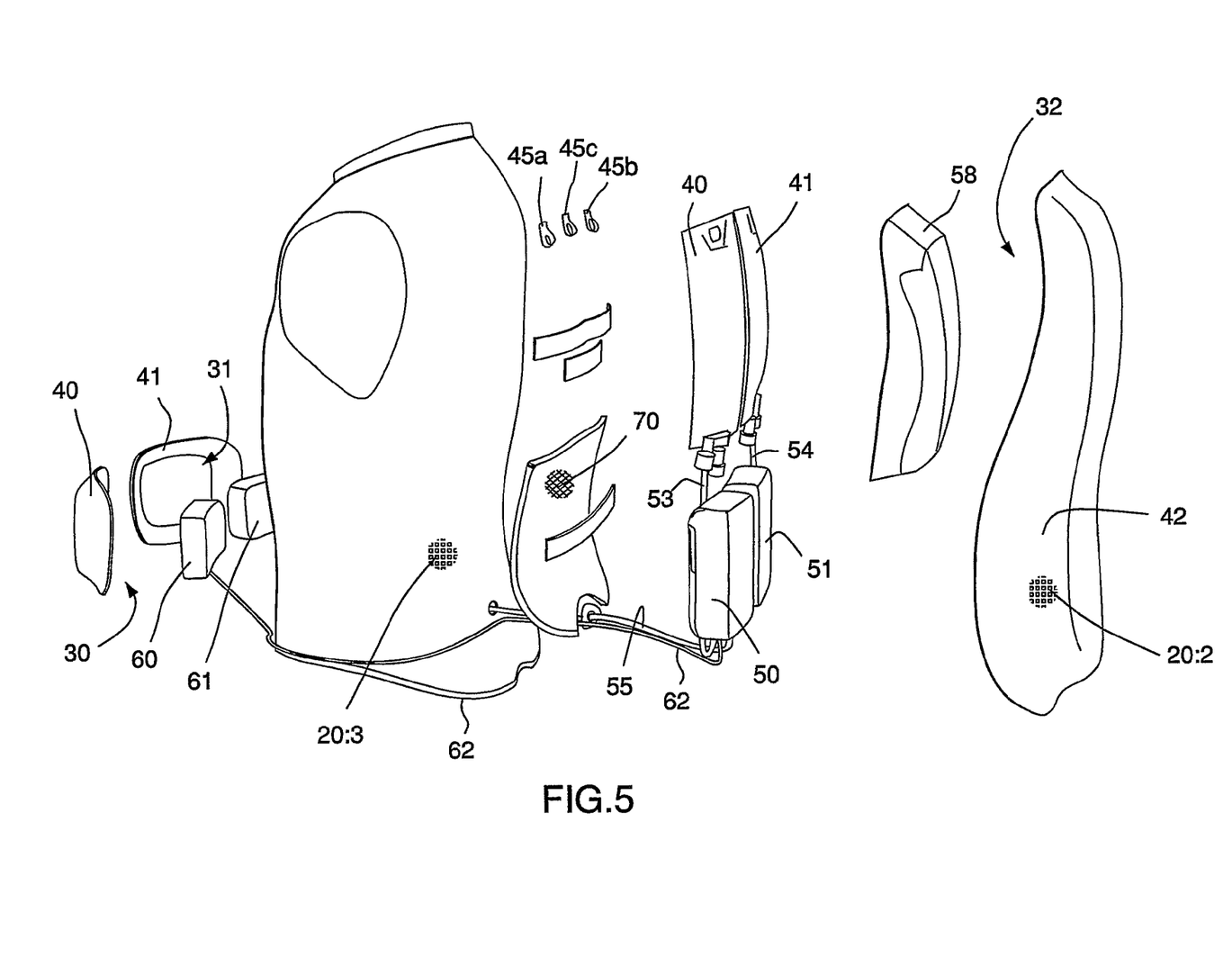
FIG. 5 shows schematically a view with separated parts of the tunic according to invention.

FIG. 5 shows the present infusion unit schematically with separated parts. The web that is intended to essentially surround the said semi-stiff parts when laid in layers is, for reasons of clarity, not shown. The tunic, as has been described above, is designed to cover the waist or trunk of the patient. The tunic is manufactured from webs that in regions are sewn in several layers located on top of each other with integrated, essentially trough-shaped and outwardly bowed spacer layers of foamed "semi-stiff" material inserted, for purposes of stiffening, into the compartment between the webs in order to form a first 30 and a second 31 storage compartment at the front piece of the tunic for the storage of batteries 60, 61 and the second storage compartment 32 at the rear piece 2. The drawing shows in more detail the first 40 and the second 41 infusion bags of the infusion unit inserted into the storage compartment 32, the holders 45a, 45b, 45c for retaining the two infusion bags suspended from an upper part of the storage compartment 32, the flexible lines 53, 54 for flow of fluid, and the first 50 and second 51 pumps in the lower part of the storage compartment 32. Between the infusion pumps 50, 51 and the web 20:3 that forms the inner web of the rear piece, i.e. the web that faces the back of the patient, there is arranged a flexible cover element 70 that is perforated such that it demonstrates high permeability to air, in order to avoid the formation of sweat and to act as insulation and damping for the two infusion pumps such that these do not disturb the patient. With reference also to FIG. 4, a shell-shaped protective cover 58 of relatively stiff plastic material, such as polycarbonate or similar, is arranged as an integrated part of the inner surface of the cover 36 with the task of, when the cover 36 is in its closed condition, protecting the two infusion bags 40, 41.

It is necessary to regulate and monitor accurately the flow of the medication into the patient during infusion treatment. If the rate of flow is not carefully controlled, a beneficial medication may have negative consequences for the patient. Selective communication between two sources of fluid for the patient is used in many cases, through the use of what are known as "multiple membrane systems" of the present type. An electrically controlled closure is in this case associated with each line element in order to provide controllable closure and opening of the flow of fluid from the relevant infusion bag. The technique of guiding fluid from the relevant fluid container is known as "fluid multiplexing". Selected quantities of fluid mix while they flow through the central outlet line 55 to the patient.

Figure 6:
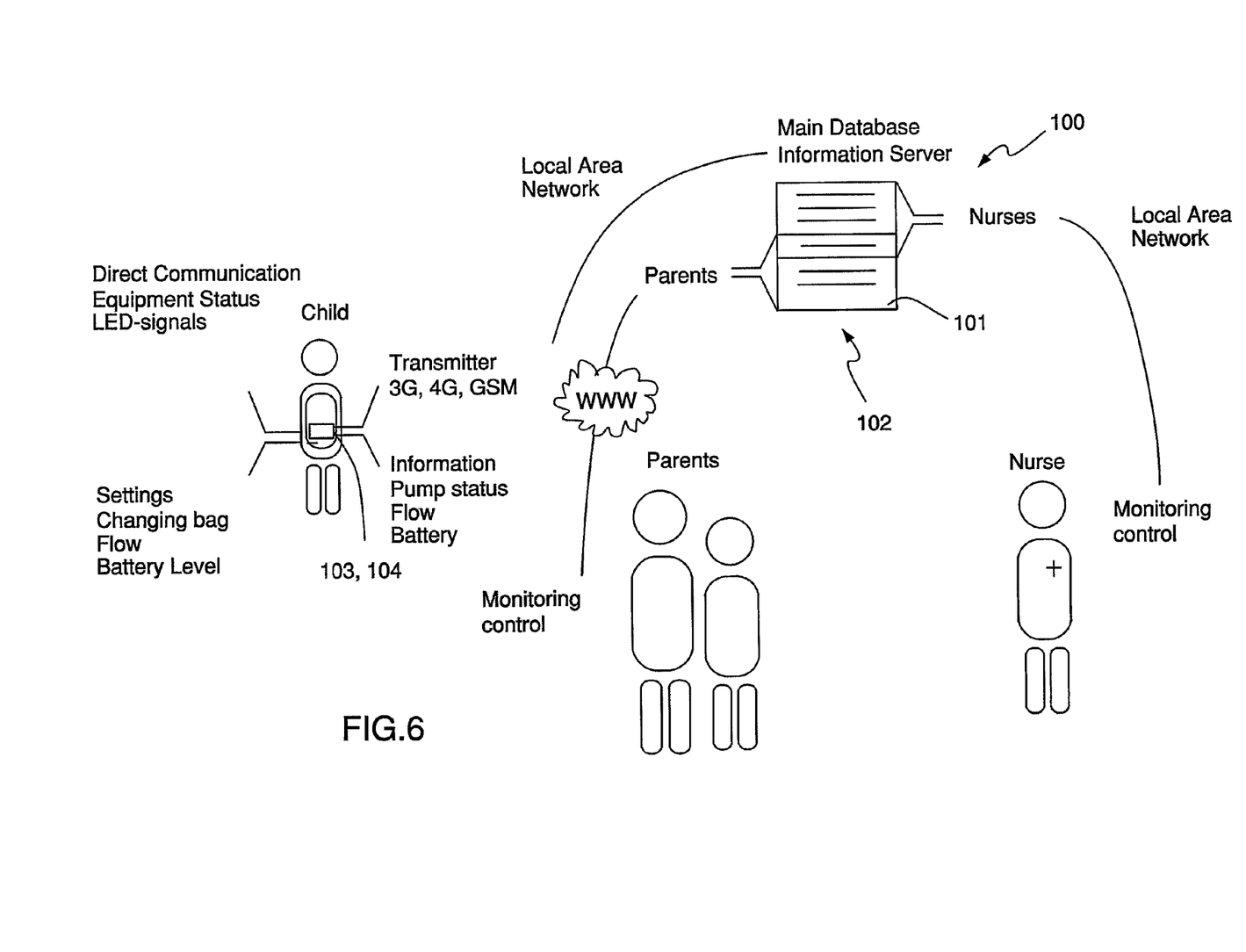
FIG. 6 shows schematically a block diagram of the various units that are components of a computer-based system for the administration of infusion therapy with the possibility for monitoring by remote control a patient who is using the tunic according to the invention.

FIG. 6 shows graphically a presentation of a monitoring system 100 for the administration of infusion therapy in which the present tunic for the administration of infusion therapy to a patient can advantageously be a component. In particular, since the present tunic allows a patient who is undergoing treatment with parenteral administration of medication to move essentially freely through the hospital. The monitoring system 100 provides the possibility of monitoring a patient by remote control, which may be particularly important in the case of a child, in order not to limit the freedom of motion of the child during the infusion therapy. The monitoring system 100 comprises a pharmacy computer 101, a central system 102, and the treatment equipment, which is integrated through a computer 103 with a radio transmitter 104 the present infusion unit that can be carried. The infusion unit is linked to the network through the computer 103 and the radio transmitter, and it can deliver real-time data to the pharmacy computer 101 of the network. The units are linked through a network 102 that allows access also through an external computer through the internet, by, for example, in the case in which the patient is a child, the parents of the child. The monitoring system 100 comprises a medication system that has been implemented as a computer program and advantageously comprises a computerised medication prescription module that makes it possible for a doctor to feed in the prescription for medication, and to monitor alarms, reminders, vital signs and results. The module monitors the prescribed medication and provides real-time data, which secures the monitoring of the medication and the dosing at the location of care i.e. directly in the treatment equipment that is integrated into the infusion unit that the patient is carrying. Thus, the administration of medication takes place directly at the location of treatment. The infusion system is designed to make the administration as efficient as possible. The infusion system provides the administrating clinician by software means with the correct medication for the patient at the correct dose at the relevant time. Prescriptions for infusion are changed often. The infusion system provides modification of the duration of infusion, the rate of flow, the site of infusion and stop orders.

It is appropriate in one alternative embodiment of the invention that data from the monitoring system 100, or directly from the computer 103 of the treatment equipment, provides the clinician with information about the status of the infusion pumps 50, 51, etc., which information about the operational status is presented directly on the infusion unit that can be carried, through, for example, a panel 59 with LEDs or control lamps 59. A green light may, for example, be the symbol in known manner that all is OK, while amber or red lights may be symbols that something is wrong, or symbols for an alarm.

The invention is not limited to that which has been described above and shown in the drawings: it can be changed and modified in several different ways within the scope of the innovative concept defined by the attached patent claims. In this part it should be understood that the tunic that is part of the infusion unit can be adapted to the patient depending on his or her age and wishes. It would be possible, for example, for the tunic to be provided with different colours, decorations or images of, for example, known comic-book figures or idols, in order to encourage children to wear the tunic.

The invention claimed is:

1. A tunic intended to be worn by a patient during infusion therapy of medication and which allows the patient to feel comfortable during treatment, the tunic comprising:
   one or more pockets configured to accommodate a combination of one or more units selected from the group of units comprised in infusion equipment that includes: infusion bags with medication, infusion pumps, batteries for driving of the infusion pumps, lines for the flow of fluid arranged between bags and pumps, and a central outlet line for the flow of fluid through a catheter to the patient,
   wherein the tunic is made of textile and each of the one or more pockets for housing a unit comprised in the infusion equipment is formed as an openable storage compartment arranged at a rear piece of the tunic, which by the action of a semi-rigid spacer layer material arranged in the textile between layers of web and having a predetermined shape, is maintained by the action of said semi-rigid spacer layer material particularly in a direction out from the tunic, and in which storage compartments the units included in the infusion equipment can be accommodated in a comfortable well-protected and discreet manner.

2. The tunic according to claim 1, whereby said openable storage compartment at the rear piece of the tunic is dimensioned to accommodate the infusion bags as well as the infusion pumps and the liquid lines for the flow of fluid from the infusion bags to the pumps.

3. The tunic unit according to any of claim 1, comprising one front piece of the tunic arranged with a first storage compartment for the batteries and second storage compartment on the rear piece of the tunic for a joint accommodation of the infusion bags and the infusion pumps.

4. The tunic according to claim 3, whereby the second storage compartment comprises holders that are arranged in the upper part of the storage compartment to support the infusion bags in a retaining manner suspended in the compartment above the infusion pumps.

5. The tunic according to claim 3, whereby the front piece of the tunic is provided with an closable access arrangement, which makes it easy to put the tunic on and to take it off.

6. The tunic according to claim 3, whereby the second storage compartment on the rear piece of the tunic is limited outwards by a cover that can be opened by folding it downwards, and which cover is provided with a releasable seal and in that said cover is in a hinge like manner anchored trough a seam or through a continuous piece of fabric at a bottom of the storage compartment.

7. The tunic according claim 1, whereby spacer layers of semi-stiff material comprise foamed cross-linkable polymer plastic and which spacer layers is similar to a core material disposed between layers of textile material.

8. The tunic according claim 1, whereby the spacer layers comprises a shell-shaped protective cover of stiff plastic material, which cover during use of the tunic protects said infusion bags.

9. The tunic according to claim 1, comprising a panel with control lamps located in a visible manner on the rear piece of the tunic that facilitates determining the current operation condition of the infusion unit that is accommodated in the tunic.

10. A method for providing infusion therapy comprising:
    providing a tunic that includes:
        one or more pockets configured to accommodate a combination of one or more units selected from the group of units comprised in infusion equipment that includes: infusion bags with medication, infusion pumps, batteries for driving of the infusion pumps, lines for the flow of fluid arranged between bags and pumps, and a central outlet line for the flow of fluid through a catheter to the patient,
        wherein the tunic is made of textile and each of the one or more pockets for housing a unit comprised in the infusion equipment is formed as an openable storage compartment arranged at a rear piece of the tunic, which by the action of a semi-rigid spacer layer material arranged in the textile between layers of web and having a predetermined shape, is maintained by the action of said semi-rigid spacer layer material particularly in a direction out from the tunic, and in which storage compartments the units included in the infusion equipment can be accommodated in a comfortable well-protected and discreet manner;
    inserting one or more articles of infusion equipment into one or more of the one or more pockets of the tunic, wherein at least one article includes a radio transmitter that is configured to supply real-time data to a pharmacy computer of a centralized system via the Internet; and
    remotely monitoring the real-time data and controlling the infusion equipment by the centralized system via Internet.

11. The tunic unit according to claim 2, comprising one front piece of the tunic arranged with a first storage compartment for the batteries and second storage compartment on the rear piece of the tunic for a joint accommodation of the infusion bags and the infusion pumps.

12. The tunic according to claim 2, whereby spacer layers of semi-stiff material comprise foamed cross-linkable polymer plastic and which spacer layers is similar to a core material disposed between layers of textile material.

13. The tunic according to claim 3, whereby spacer layers of semi-stiff material comprise foamed cross-linkable polymer plastic and which spacer layers is similar to a core material disposed between layers of textile material.

14. The tunic according to claim 4, whereby spacer layers of semi-stiff material comprise foamed cross-linkable polymer plastic and which spacer layers is similar to a core material disposed between layers of textile material.

15. The tunic according to claim 2, whereby the spacer layers comprises a shell-shaped protective cover of stiff plastic material, which cover during use of the tunic protects said infusion bags.

16. The tunic according to claim 3, whereby the spacer layers comprises a shell-shaped protective cover of stiff plastic material, which cover during use of the tunic protects said infusion bags.

17. The tunic according to claim 4, whereby the spacer layers comprises a shell-shaped protective cover of stiff plastic material, which cover during use of the tunic protects said infusion bags.

18. The tunic according to claim 2, comprising a panel with control lamps located in a visible manner on the rear piece of the tunic that facilitates determining the current operation condition of the infusion unit that is accommodated in the tunic.

19. The tunic according to claim 3, comprising a panel with control lamps located in a visible manner on the rear piece of the tunic that facilitates determining the current operation condition of the infusion unit that is accommodated in the tunic.

20. The tunic according to claim 4, comprising a panel with control lamps located in a visible manner on the rear piece of the tunic that facilitates determining the current operation condition of the infusion unit that is accommodated in the tunic.

\* \* \* \* \*